(12) United States Patent
Karli et al.

(10) Patent No.: US 11,340,212 B2
(45) Date of Patent: May 24, 2022

(54) BIOLOGICAL FLUID COMPOSITION CATEGORIZATION METHOD

(71) Applicant: Greyledge Technologies, LLC, Avon, CO (US)

(72) Inventors: David Karli, Avon, CO (US); Theodore Sand, Avon, CO (US)

(73) Assignee: Greyledge Technologies, LLC, Avon, CO (US)

( * ) Notice: Subject to any disclaimer, the term of this patent is extended or adjusted under 35 U.S.C. 154(b) by 307 days.

(21) Appl. No.: 15/958,991

(22) Filed: Apr. 20, 2018

(65) Prior Publication Data

US 2018/0306773 A1 Oct. 25, 2018

Related U.S. Application Data

(60) Provisional application No. 62/488,229, filed on Apr. 21, 2017.

(51) Int. Cl.
*G01N 33/49* (2006.01)
*G01N 33/15* (2006.01)

(52) U.S. Cl.
CPC .......... *G01N 33/492* (2013.01); *G01N 33/15* (2013.01)

(58) Field of Classification Search
CPC .............................. G01N 33/492; G01N 33/15
See application file for complete search history.

(56) References Cited

U.S. PATENT DOCUMENTS

| | | | | |
|---|---|---|---|---|
| 2010/0092444 A1* | 4/2010 | Mishra | ...................... | A61P 9/00 424/93.71 |
| 2014/0356893 A1* | 12/2014 | Mishra | ................. | C12N 5/0644 435/29 |

OTHER PUBLICATIONS

Commercial Separation Systems Designed for Preparation of Platelet Rich Plasma Yield Differences in Cellular Composition Ryan M Degen, Jonathan A Bernard Kristin S Oliver, Joshua S Dines HSSJ (2017) 13: 75-80 (Year: 2016).*

* cited by examiner

*Primary Examiner* — Brian R Gordon
*Assistant Examiner* — Dwan A Gerido
(74) *Attorney, Agent, or Firm* — Winstead PC

(57) ABSTRACT

Methods of analyzing a biological fluid to determine an expected therapeutic benefit of the fluid include determining amounts of components within the biological fluid. Comparisons of a first component of the biological fluid relative to another component of the biological are made to characterize a therapeutic effect of the biological fluid.

7 Claims, 6 Drawing Sheets

BIOLOGICAL FLUID COMPOSITION CATEGORIZATION METHOD

CROSS-REFERENCES TO RELATED APPLICATIONS

This Application claims the benefit under 35 U.S.C. § 119(e) of U.S. Provisional Patent Application No. 62/488,229 filed Apr. 21, 2017, which is incorporated herein by reference in its entirety as if fully set forth herein.

BACKGROUND

Platelet-rich plasma (PRP), a biological fluid obtained by centrifuging whole blood and collecting therefrom a "platelet portion," contains a variety of cellular components including: platelets (Plts), red blood cells (RBCs), white blood cells (WBCs), and a sub-type of WBC, neutrophils (Neu), as well as other types of nucleated cells. The complex composition of PRP presents a challenge when attempting to characterize a potential therapeutic benefit of PRP preparations. Plts are a source of growth factors that contribute to the therapeutic benefit of PRP, but RBCs and WBCs (especially the Neu) are associated with a negative contribution, including promoting inflammation and pain at the injection site. While it is possible to count each of these components, the resulting data set is cumbersome and doesn't provide a direct answer to the question about a therapeutic potential of a particular PRP preparation.

Current strategies to characterize PRP preparations include the following approach:

| Type   | White Blood Cells       | Activated? |
|--------|-------------------------|------------|
| Type 1 | Increased over Baseline | No         |
| Type 2 | Increased over Baseline | Yes        |
| Type 3 | Minimal or no WBCs      | No         |
| Type 4 | Minimal or no WBCs      | Yes        |

A: >5× Platelets
B: <5× Platelets

In the above scheme, PRP can be categorized in terms of being above or below a 5-fold increase in Plts in the PRP compared to the source material whole blood. There is a consideration of the level of WBCs, but there is no indication what it means to have minimal WBCs. A PRP preparation with no WBCs is virtually impossible to achieve due to casual aggregation and stickiness of Plts and WBCs. One of the limitations of this classification scheme is that it is focused on the device or system operating parameters used to produce a PRP preparation instead of creating a comprehensive characterization of the critical components of an individual patient's PRP preparation.

A similar strategy to characterize PRP preparations includes a specification that the PRP include a cutoff of 1% for the presence of WBCs and a 1% cutoff for RBC content. Thus, a "depleted" PRP sample will have no more than 1% of either RBC or WBCs. This approach includes a consideration of the actual component values from a patient's PRP preparation, but uses the information to sort the preparation into a binary characterization.

Both of these schemes represent attempts to provide a more quantitative approach to the characterization of PRP but both schemes depend on a set of binary choices, which is more reflective of the device/system that produced the PRP preparation as opposed to providing detailed information on the therapeutic potential of the patient's PRP preparation.

SUMMARY

Embodiments of the invention comprise analyzing a biological fluid. In some embodiments, the biological fluid may be processed prior to the analyzing to isolate particular components of interest. The analyzing includes determining amounts or concentrations of components of the biological fluid. In some embodiments, the analyzing is done with a fluid analyzer, such as a hemoanalyzer. In some embodiments, one or more of the components may be categorized as having a positive therapeutic effect or a negative therapeutic effect. Comparisons of a first component of the biological fluid relative to another component of the biological are made to predict a therapeutic effect of the biological fluid. For example, a ratio of a first component of the biological fluid relative to a second component of the biological fluid may be determined. The resulting ratio provides an indication of a therapeutic effect of the biological fluid. In some embodiments, the biological fluid is further analyzed by determining a product of two determined ratios. The resulting product provides a more complete understanding of an expected therapeutic effect of the biological fluid. In some embodiments, a product of three ratios is determined. The resulting products provide a more complete understanding of an expected therapeutic effect of the biological fluid.

Various biological fluids may be analyzed using the methods disclosed herein. In some embodiments the biological fluid is a PRP preparation that is isolated from blood. In other embodiments, the biological fluid is a stromal vascular fraction (SVF) that is isolated from adipose tissue or bone marrow concentrate (BMC) obtained from aspiration of bone marrow.

In some embodiments, the methods described herein provide ways of characterizing a PRP preparation with regard to a possible therapeutic potential of the preparation. The proposed invention provides for a way to characterize PRP preparations in terms of continuous values. Continuous values are more representative of the complex nature of PRP preparations, since the ratios relate the concentration (number) of Plts to the concentration (number) of RBCs, WBCs, and Neu. The inventive method also can be used to provide insight into the therapeutic potential of a PRP preparation, since the values of the ratio of Plt to RBCs, WBCs, or Neu can be less than 1, equal to 1, or greater than 1. Values greater than 1 mean that there are more Plts present in the PRP preparation for each RBC, WBC, or Neu present in the preparation. Since PRP's therapeutic potential is associated with the PRP's Plt content, the higher the ratio's value the greater the number of Plts in comparison to the other components. Consequently, a larger value of the ratios, as determined by applying the inventive method, directly implies a larger therapeutic potential of the PRP preparation. The value of these ratios reflects the composition of the patient's PRP in a condensed format, and the individual patient values for the inventive ratios are available for use as a guide to the patient's therapy, and for comparison with clinical outcomes recorded after the patient is treated. An additional benefit of the inventive method of ratios is that this approach is not limited to comparing Plts, RBCs, WBCs, and Neutrophils, but can be applied to pairs of components present in the processed biological fluid for which analytical results are available.

After a therapeutic potential of a biological fluid has been determined, the biological fluid may be used to treat a patient. In some embodiments, the therapeutic potential must exceed a predetermined or threshold value to be used as a patient treatment.

BRIEF DESCRIPTION OF THE DRAWINGS

For a more complete understanding of the present invention and for further objects and advantages thereof, reference may now be had to the following description taken in conjunction with the accompanying drawings in which.

DETAILED DESCRIPTION

Figure 1:
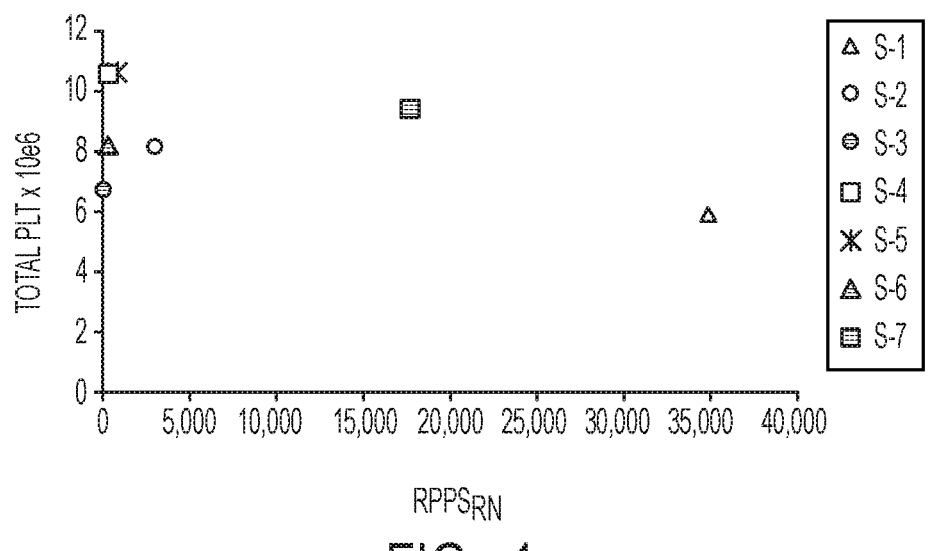
FIG. 1 is a graph of total Plt versus regenerative potential platelet score-RN for 7 PRP-Producing Systems.

Various embodiments of the present invention will now be described more fully with reference to the accompanying drawings. The invention may, however, be embodied in many different forms and should not be construed as limited to the embodiments set forth herein.

When analyzing whole blood, a preparation of PRP is prepared. By way of example, the following parameters of the PRP preparation are determined (additional parameters may be calculated):

(Plt concentration)/(RBC concentration)       Platelet RBC Ratio (PRR):

(Plt concentration)/(WBC concentration)       Platelet WBC Ratio (PRW):

(Plt concentration)/(Neu concentration)       Platelet Neutrophil Ratio (PRN):

The concentrations of the above identified components can be determined by the use of a specialized instrument commonly referred to as a hemoanalyzer. This type of instrument (e.g., Abbott's Diagnostics Cell Dyn Ruby) provides a multi-parametric analysis of whole blood samples, including a differential analysis of the WBCs present, which provides a count of Neus, as well as a count of Plts and RBCs.

Once a component analysis has been performed, individual values of the Plts, RBCs, WBCs, and neutrophils can be placed into formulas to calculate the resulting ratios. As a result of calculating these ratios, it is possible to characterize the therapeutic potential of the PRP preparation, since the higher the value for a ratio, the higher the excess of Plts over the denominator component. For example, if a PRW has a value of 500, it means that the procedure to produce the PRP resulted in a preparation with 500 platelets for each WBC present. Since WBCs (including neutrophils) and RBCs have been reported to have negative consequences when injected, a higher value of the inventive ratios implies that the PRP preparation should have a greater therapeutic potential.

Another aspect of the inventive method of ratios involves determining a product of the inventive ratios to create the following Regenerative Potential Platelet Scores (RPPS), among others:

$$RPPS_{RN}=(PRR)\times(PRN) \text{ for Neutrophil ratios}$$

$$RPPS_{RW}=(PRR)\times(PRW) \text{ for WBC ratios}$$

Values of the RPPS also are indicative of the therapeutic potential of the PRP since the RPPS combines both of the ratios of Plts with RBCs and Plts with either WBC or Neu. Thus, the RPPS value includes both the positive therapeutic contributor, Plts, as well as two of the negative components (either RBC and WBC, or RBC and Neu). As with the ratios themselves, a higher numeric value of the RPPS implies that the PRP preparation will have a higher therapeutic potential.

In another embodiment, the $RPPS_{RNW}$ can be created as follows:

$$RPPS_{RNW}=(PRR)\times(PRW)\times(PRN)$$

In this $RPPS_{RNw}$, ratios of all three negative components are linked in a single value along with the PRP's Plt content. The $RPPS_{RNw}$ value provides an indication of an expected therapeutic potential of the PRP preparation.

WORKING EXAMPLE

Various values of ratios and the RPPS were calculated using data obtained from a study by Degen, et al. (2017). Degen R M, Bernard J A, Oliver K S, et al. Commercial Separation Systems Designed for Preparation of Platelet-Rich Plasma Yield Differences in Cellular Composition. HSS J 2017; 13:75-80. As described in Degen, the average concentrations of Plts, WBCs, RBCs and Neutrophils were determined by splitting and processing seven whole blood samples from unrelated human donors in six commercially available PRP systems. The average volume of the PRP produced with each system was recorded. The data, including calculated values of PRW, PPR, PRN, $RPPS_{RN}$, $RPPS_{RW}$, and $RPPSR_{NW}$, is presented in Table 1. The data shown for S-7 was obtained by a review of hemoanalytic data on 25 patients following a manual processing of the patients' whole blood to create PRP preparations.

TABLE 1

PRP Component Values for Systems Producing PRP and Ratios

| Sys. | Avg. Vol. | WBC (10e3) | RBC (10e6) | Neu (10e3) | Plt (10e3) | Avg. Total Plt | PRW | PPR | PRN | $RPPS_{RN}$ | $RPPS_{RW}$ | $RPPS_{RNW}$ |
|---|---|---|---|---|---|---|---|---|---|---|---|---|
| S-1 | 2.9  | 11.0 | 0.2 | 0.6 | 2,064.0 | 5.99E+09 | 187.6 | 10.3 | 3,440.0 | 35,500.8 | 1,936.4 | 6.87E+07 |
| S-2 | 3.5  | 16.9 | 1.0 | 1.8 | 2,310.0 | 8.09E+09 | 136.7 | 2.3  | 1,283.3 | 2,964.5  | 315.7   | 9.36E+05 |
| S-3 | 6.0  | 20.6 | 3.1 | 7.4 | 1,129.0 | 6.77E+09 | 54.8  | 0.4  | 152.6   | 55.6     | 20.0    | 1.11E+03 |
| S-4 | 7.0  | 22.9 | 3.2 | 4.2 | 1,508.0 | 1.06E+10 | 65.9  | 0.5  | 359.0   | 169.2    | 31.0    | 5.25E+05 |
| S-5 | 5.3  | 19.8 | 1.1 | 4.1 | 1,989.0 | 1.05E+10 | 100.5 | 1.8  | 485.1   | 877.2    | 181.6   | 1.59E+05 |
| S-6 | 6.1  | 27.3 | 1.0 | 9.4 | 1,343.0 | 8.19E+09 | 49.2  | 1.3  | 142.9   | 191.9    | 66.1    | 1.27E+04 |
| S-7 | 10.6 | 1.5  | 0.1 | 0.4 | 886.6   | 9.40E+09 | 611.4 | 8.9  | 2,015.0 | 17,865.0 | 5,421.1 | 9.68E+07 |

Figure 2:
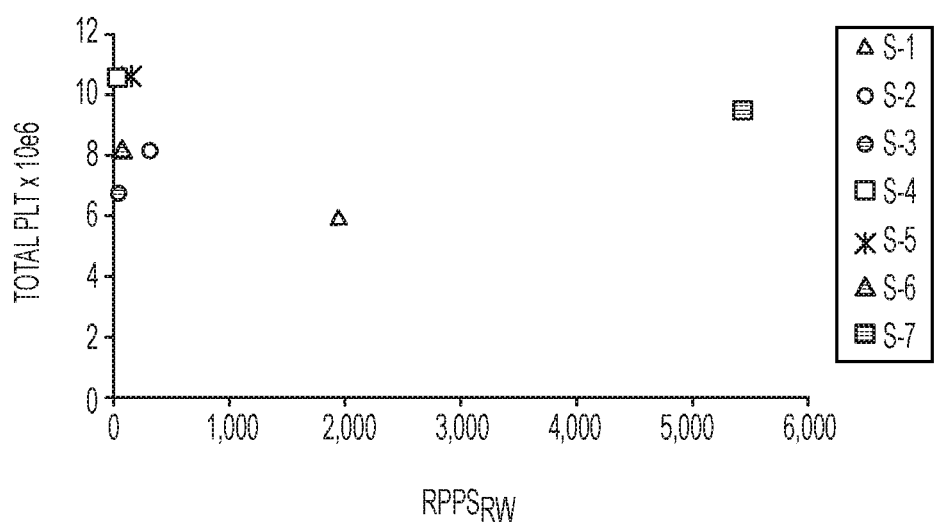
FIG. 2 is a graph of total Plt versus regenerative potential platelet score-RW for 7 PRP-Producing Systems.

The calculated data for $RPPS_{RN}$ and $RPPS_{RW}$ versus the Total Platelets obtained for each system are plotted in FIGS. 1 and 2, respectively. As shown in FIGS. 1 and 2, the two Regenerative Potential Platelet Scores reflect significant differences among the various processing systems. Some systems, for example S-4 and S-5, show high Total Platelets, but very low ratios of Plts to either WBC or Neutrophil levels. In contrast, S-1 shows very high ratios of Plts to either WBC or Neutrophil levels, but has the lowest yield of Total Plts of the seven systems evaluated. Thus, the inventive method provides a way to identify an expected therapeutic potential of a PRP preparation that is not readily apparent by simply looking at data of the individual components.

In other embodiments, the method of ratios can be applied to biological fluids other than PRP, including the stromal vascular fraction (SVF) isolated from a patient's adipose tissue and bone marrow concentrate (BMC) obtained from a bone marrow aspiration. Choices for the numerators and denominators of the inventive ratios for processed, biological fluids other than PRP reflect the specific cellular components found in the biological fluid.

For example, mesenchymal stem cells (MSCs) and hematopoietic stem cells (HSCs) are present in bone marrow and would be concentrated in a patient's BMC. The Stem Cell Ratio (SCR) can be defined as follows:

$SCR_{HM}$=(HSC number or concentration)/(MSC number or concentration)

The values of other components might be appropriate to be used in the numerator of the ratio, while the denominator remains a stem cell component. For example, BMC contains variable levels of Plts, so the following two ratios can be used as an indicator of therapeutic potential for a BMC treatment:

$SCR_{PM}$=(Plt number or concentration)/(MSC number or concentration)

$SCR_{PH}$=(Plt number or concentration)/(HSC number or concentration)

For SVF, components include total nucleated cells (TNC), monocytes, immature granulocytes (IG), Plts, WBC, and RBC. SVF ratios of interest include:

$SVF_{PM}$=(Plt number or concentration)/(monocyte number or concentration)

$SVF_{PIG}$=(Plt number or concentration)/(IG number or concentration)

$SVF_{WBCRSC}$=(WBC number or concentration)/(RBC number or concentration)

$SVF_{INCRBC}$=(TNC number or concentration)/(RBC number or concentration)

Plots of Total Platelets Versus Ratios

Figure 3A:
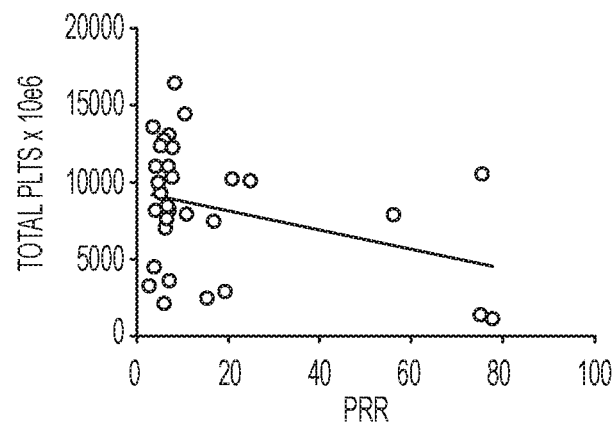
FIG. 3A is a graph of total Plt versus platelet RBC ratio for a PRP preparation.
Figure 3B:
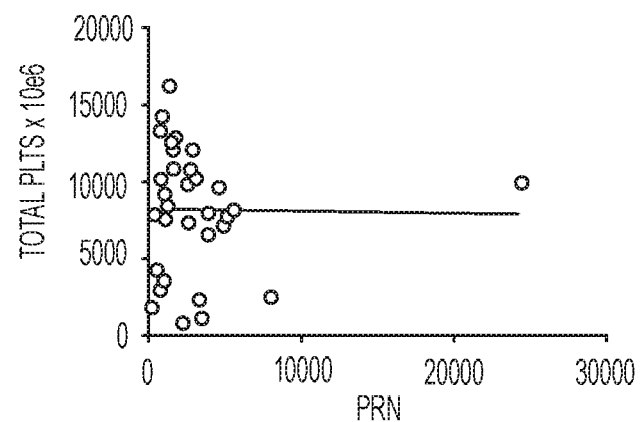
FIG. 3B is a graph of total Plt versus platelet neutrophil ratio for a PRP preparation.
Figure 3C:
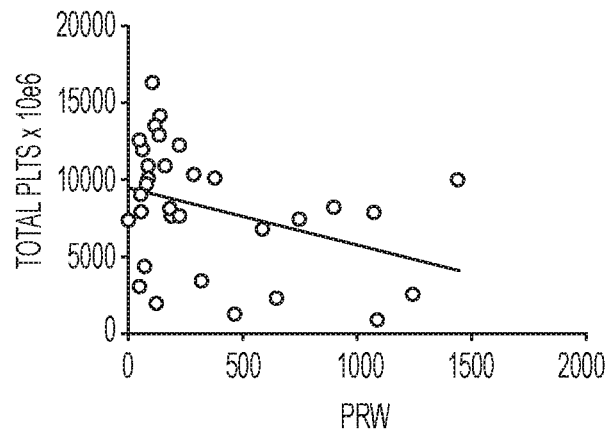
FIG. 3C is a graph of total Plt versus platelet WBC ratio for a PRP preparation.

In some embodiments, total platelet level of a PRP sample is useful in plotting ratios since it is the platelet content that is the key therapeutic component in PRP. FIGS. 3A-3C are graphs showing ratios for 32 PRP preparations used to treat patients. Linear regression lines illustrate trends in the data, but are not statistically significantly different from 0. Despite the use of a standard processing protocol, the values of the ratios varied widely among the patients.

Figure 4A:
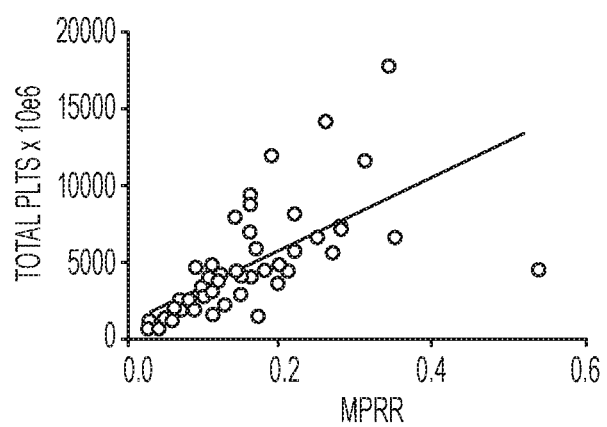
FIG. 4A is a graph of total Plt versus marrow platelet ratio RBC for a BMC preparation.
Figure 4B:
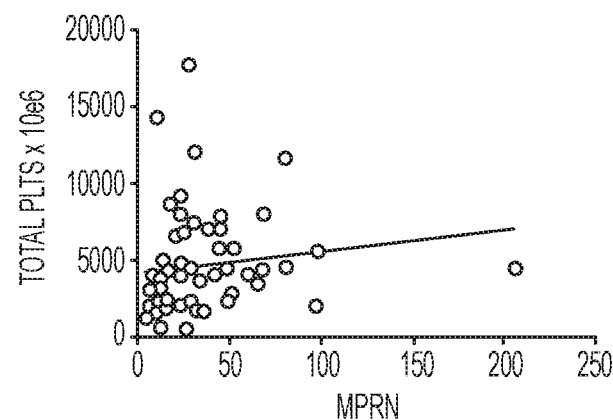
FIG. 4B is a graph of total Plt versus marrow platelet ratio NEU for a BMC preparation.
Figure 4C:
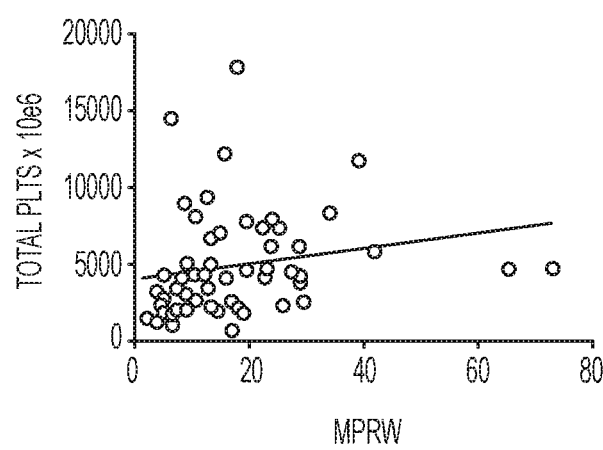
FIG. 4C is a graph of total Plt versus marrow platelet WBC for a BMC preparation.

FIGS. 4A-4C are graphs showing ratios calculated for 57 BMC preparations used to treat patients. Linear regression lines illustrate trends in the data. FIG. 4A shows a positive trend (which is statistically different from a slope of 0) in which a higher ratio of Plts per RBC indicates a more efficient retention of Plts. In contrast, FIG. 3A shows a slightly negative trend where lower total Plts are obtained with higher ratios of Plts per RBC. This difference probably is associated with the detailed protocol used to produce PRP preparations, which results in a greatly reduced RBC and leukocyte content, while the method to produce BMC intentionally recovers the upper portion of the RBC layer. Thus, the distinctly different protocols may influence efficiency for retaining Plts in the processing steps to produce PRP and BMC.

Another benefit of calculating ratios is that it is possible to compare average yields of the critical components when using a device technology to generate PRP. A recent publication by Degen, et al. (2017) has the requisite hemoanalytic data set for 6 commercial PRP systems, derived from processing whole blood from seven unrelated donors. Data for ratios associated with the 32 PRP preparations produced with a manual method was averaged and is included as S-7.

Figure 5A:
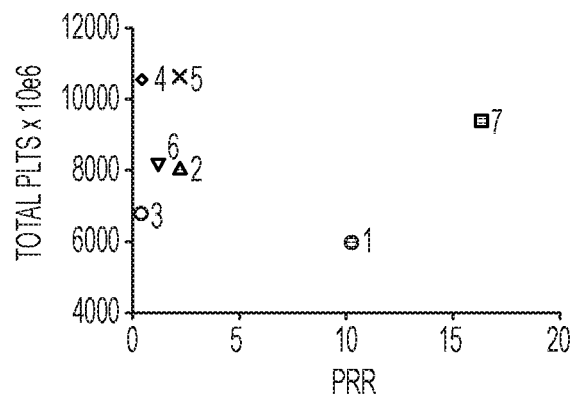
FIG. 5A is a graph of total Plt versus platelet RBC ratio for a commercial PRP system.
Figure 5B:
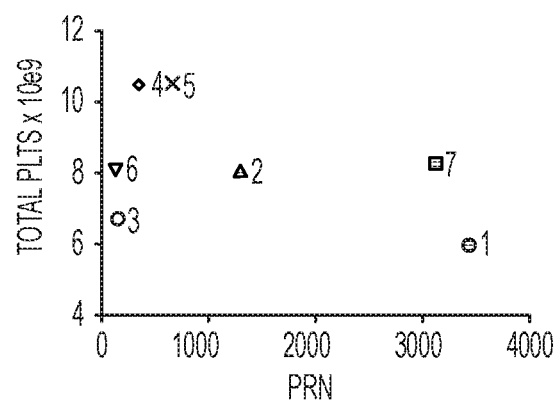
FIG. 5B is a graph of total Plt versus platelet neutrophil ratio for a commercial PRP system.
Figure 5C:
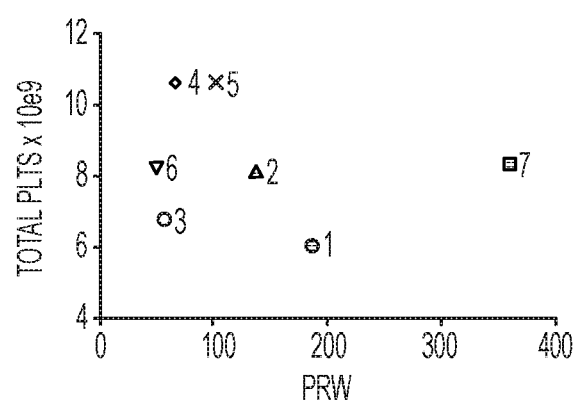
FIG. 5C is a graph of total Plt versus platelet WBC ratio for a commercial PRP system.

As shown in FIGS. 5A-5C, there are wide variations in the ratios associated with the different device technologies. In FIGS. 5A-5C, data points are numbered 1-7 to correspond with the following samples: S-1: Arthrex Angel System-2% Hct, S-2: Arthrex Angel System-7% Hct, S-3: Emcyte, S-4: Harvest, S-5: Arteriocyte, S-6: Biomet, S-7: Manual method used at the Steadman Clinic. Part of the difference results from the manufacturers' instructions for using their devices, since some protocols involve two spins, while others involve one spin. It also is evident that the seven systems operate with different efficiencies in reducing the levels of NEUs and WBCs. For example, S-1 provides the highest value for the PRN, but shifts to the second highest for the PRW.

In other embodiments, any of the various ratios described herein can be generated either manually or in an electronic manner. For example, values obtained from a component analysis of a patient's biological fluid can be entered into a calculating program to produce one or more of the ratios shown above. The automatic calculation and display of one or more of the ratios provide a facile method for data review, either by a medical professional or for entry into an outcomes-based tracking software (e.g., RedCap, Vanderbilt University, Nashville, Tenn.).

In some embodiments, after a possible therapeutic potential or benefit of a sample has been determined, there may be a desire to increase a Plt content of the sample. This is accomplished by collecting more sample to make an additional preparation. The original preparation and the additional preparation may be combined to increase Plt concentration. For example, the Plt value of a BMC preparation may be increased by processing a whole blood sample and combining the processed whole blood sample with the BMC preparation. For an SVF preparation, it may be determined that a platelet rich matrix (PRM) is low. A PRP preparation may be produced and combined with the SVF to raise the PRM value.

Although various embodiments of the method and system of the present invention have been illustrated in the accompanying Drawings and described in the foregoing Specification, it will be understood that the invention is not limited to the embodiments disclosed, but is capable of numerous rearrangements, modifications, and substitutions without departing from the spirit and scope of the invention as set forth herein. For example, various fractions are identified above. It should be understood that other components of preparations could be used to calculate other fractions or ratios. It is intended that the Specification and examples be considered as illustrative only.

What is claimed is:

1. A method of analyzing a platelet-rich plasma sample, the method comprising:
    analyzing the platelet-rich plasma sample, with a fluid analyzer, to determine a concentration of a first component of the platelet-rich plasma sample and a second component of the platelet-rich plasma sample, wherein the first component comprises platelets and the second component comprises red blood cells;
    determining, with the fluid analyzer, a ratio of the first component to the second component;
    responsive to a determination by the fluid analyzer that the ratio of the first component to the second component is less than one, increasing the ratio of the first component to the second component by adding more of the first component to the platelet-rich plasma sample and preparing a patient treatment with the platelet-rich plasma sample;
    analyzing, with the fluid analyzer, the platelet-rich plasma sample to determine a concentration of a third component of the platelet-rich plasma sample, wherein the third component comprises white blood cells;
    determining a product of two or more of the first, second, and third components; and
    responsive to a determination that the ratio of the first component to the second component is greater than or equal to one, preparing the patient treatment with the platelet-rich plasma sample.

2. The method of claim 1, further comprising:
    analyzing, with the fluid analyzer, the platelet-rich plasma sample to determine a concentration of a fourth component of the platelet-rich plasma sample, wherein the fourth component comprises neutrophils.

3. The method of claim 2, further comprising determining the product of the concentration of the first component and the concentration of the second component.

4. The method of claim 2, further comprising determining the product of the concentration of the first component and the concentration of the third component.

5. The method of claim 2, further comprising determining the product of the concentration of the first component, the concentration of the second component, and the concentration of the third component.

6. The method of claim 1, wherein the fluid analyzer is a hemoanalyzer.

7. The method of claim 1, further comprising treating a patient with the patient treatment.

* * * * *